US00PP25393P2

(12) United States Plant Patent
Arts

(10) Patent No.: US PP25,393 P2
(45) Date of Patent: Mar. 31, 2015

(54) ***HYDRANGEA* PLANT NAMED 'HBAMARI'**

(50) Latin Name: *Hydrangea macrophylla*
Varietal Denomination: HBAmari

(71) Applicant: Niels Arts, Aalsmeer (NL)

(72) Inventor: Niels Arts, Aalsmeer (NL)

(73) Assignee: Hydrangea Breeders Association B.V., De Kwakel (NL)

( * ) Notice: Subject to any disclaimer, the term of this patent is extended or adjusted under 35 U.S.C. 154(b) by 137 days.

(21) Appl. No.: 13/815,890

(22) Filed: Mar. 15, 2013

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Annette Para
(74) *Attorney, Agent, or Firm* — C. A. Whealy

(57) ABSTRACT

A new and distinct cultivar of *Hydrangea* plant named 'HBAmari', characterized by its upright and somewhat outwardly spreading plant habit; vigorous growth habit; strong and sturdy stems; freely flowering habit; and large inflorescences with numerous violet blue-colored sterile flowers.

1 Drawing Sheet

Botanical designation: *Hydrangea macrophylla.*
Cultivar denomination: 'HBAmari'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HBAmari'.

The new *Hydrangea* plant is a product of a planned breeding program conducted by the Inventor in De Kwakel, The Netherlands. The objective of the breeding program was to create new freely-branching *Hydrangea* plants with strong and sturdy stems, large inflorescences, attractive flower color and good postproduction longevity.

The new *Hydrangea* plant originated from a cross-pollination made by the Inventor in April, 2007 in De Kwakel, The Netherlands, of a proprietary selection of *Hydrangea macrophylla* identified as code number 202122-002, not patented, as the female, or seed, parent with a proprietary selection of *Hydrangea macrophylla* identified as code number 203243-006, not patented, as the male, or pollen, parent. The new *Hydrangea* plant was discovered and selected by the Inventor as a single flowering plant from within the progeny of the stated cross-pollination in a controlled greenhouse environment in De Kwakel, The Netherlands in March, 2009.

Asexual reproduction of the new *Hydrangea* plant by vegetative cuttings in a controlled environment in De Kwakel, The Netherlands since June, 2009 has shown that the unique features of this new *Hydrangea* plant are stable and reproduced true to type in successive generations.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'HBAmari'. These characteristics in combination distinguish 'HBAmari' as a new and distinct *Hydrangea* plant:

1. Upright and somewhat outwardly spreading plant habit.
2. Vigorous growth habit.
3. Strong and sturdy stems.
4. Freely flowering habit.
5. Large inflorescences with numerous violet blue-colored sterile flowers.

Plants of the new *Hydrangea* can be compared to plants of the female parent selection. Plants of the new *Hydrangea* differ primarily from plants of female parent selection in the following characteristics:

1. Plants of the new *Hydrangea* are more vigorous than plants of the female parent selection.
2. Plants of the new *Hydrangea* have longer and thicker lateral branches than plants of the female parent selection.

Plants of the new *Hydrangea* can be compared to plants of the male parent selection. Plants of the new *Hydrangea* differ primarily from plants of male parent selection in the following characteristics:

1. Plants of the new *Hydrangea* are more vigorous than plants of the male parent selection.
2. Plants of the new *Hydrangea* have thicker lateral branches than plants of the male parent selection.
3. Plants of the new *Hydrangea* and the male parent selection differ in sterile flower color as plants of the male parent selection have light blue-colored sterile flowers.

Plants of the new *Hydrangea* can be compared to plants of the *Hydrangea hybrida* 'Elbtal', not patented. In side-by-side comparisons conducted in Glandorf, Germany, plants of the new *Hydrangea* differed from plants of 'Elbtal' in the following characteristics:

1. Plants of the new *Hydrangea* had thicker and stronger lateral branches than plants of 'Elbtal'.
2. Plants of the new *Hydrangea* had larger inflorescences than plants of 'Elbtal'.

3. Plants of the new *Hydrangea* and 'Elbtal' differed in sterile flower color as plants of 'Elbtal' had light blue-colored sterile flowers.

BRIEF DESCRIPTION OF THE PHOTOGRAPH

The accompanying colored photograph illustrates the unique appearance of the new *Hydrangea* plant showing the colors as true as it is reasonably possible to obtain in colored reproductions of this type. Colors in the photograph may differ from the color values cited in the detailed botanical description which accurately describe the colors of the new *Hydrangea* plant.

The photograph comprises a side perspective view of a typical inflorescence and leaves of 'HBAmari'.

DETAILED BOTANICAL DESCRIPTION

Plants used in the aforementioned photograph and in the following description were grown during the spring and summer in 17-cm containers in a glass-covered greenhouse in De Kwakel, The Netherlands and under cultural practices typical of commercial *Hydrangea* production. During the production of the plants, day and night temperatures averaged 17° C. Soil acidity was adjusted to a pH level of 4 with aluminum sulfate to enhance blue coloration of the flowers. Plants were pinched one time. Plants of the new *Hydrangea* were one year old when the photograph and description were taken. In the following description, color references are made to The Royal Horticultural Society Colour Chart, 1995 Edition, except where general terms of ordinary dictionary significance are used.

Botanical description: *Hydrangea macrophylla* 'HBAmari'.

Parentage:

*Female, or seed, parent*.—Proprietary selection of *Hydrangea macrophylla* identified as code number 202122-002, not patented.

*Male, or pollen, parent*.—Proprietary selection of *Hydrangea macrophylla* identified as code number 203243-006, not patented.

Propagation:

*Type cutting*.—By vegetative cuttings.

*Time to initiate roots, summer*.—About two weeks at temperatures about 23° C.

*Time to initiate roots, winter*.—About 18 days at temperatures about 18° C.

*Time to produce a rooted young plant, summer*.—About four weeks at temperatures about 23° C.

*Time to produce a rooted young plant, winter*.—About five weeks at temperatures about 18° C.

*Root description*.—Thick; whitish brown in color.

*Rooting habit*.—Freely branching; dense.

Plant description:

*Plant and growth habit*.—Upright to somewhat outwardly spreading plant habit; rounded in shape; strong and sturdy stems; rapid growth rate and vigorous growth habit.

*Plant height*.—About 80 cm.

*Plant diameter* (*spread*).—About 50 cm.

Lateral branch description:

*Branching habit*.—Freely branching habit with about five lateral branches per plant.

*Length*.—About 80 cm.

*Diameter*.—About 1 cm.

*Internode length*.—About 4.5 cm to 8.5 cm.

*Stem texture*.—Smooth, glabrous.

*Strength*.—Strong, sturdy.

*Color*.—Close to 144B overlain with close to 187A.

Leaf description:

*Arrangement*.—Opposite, simple.

*Length*.—About 17 cm.

*Width*.—About 13 cm.

*Shape*.—Ovate.

*Apex*.—Acute.

*Base*.—Obtuse.

*Margin*.—Dentate.

*Texture, upper surface*.—Smooth to rugose, glabrous.

*Texture, lower surface*.—Rugose, glabrous.

*Venation pattern*.—Pinnate.

*Color*.—Developing and fully expanded leaves, upper surface: Close to 147A; venation, close to 146D. Developing and fully expanded leaves, lower surface: Close to 137C; venation, close to 148C.

*Petiole*.—Length: About 3.5 cm to 4 cm. Diameter: About 6 mm. Texture, upper and lower surfaces: Smooth, glabrous. Color, upper and lower surfaces: Close to 144B.

Flower description:

*Flower type and habit*.—Single rounded sterile and small inconspicuous ovate-shaped fertile flowers arranged on mophead-type terminal panicles; panicles globular in shape; flowers face upright to outwardly.

*Fragrance*.—None detected.

*Natural flowering season*.—Short production time as a cooling treatment is not required for flower development; continuous flowering during the summer in Northern Europe.

*Flower longevity*.—Sterile flowers last about four months on the plant, sterile flowers persistent; fertile flowers last about one month on the plant, fertile flowers not persistent; as a cut flower, inflorescences maintain good substance for about three weeks.

*Quantity of flowers*.—Freely flowering habit; about 100 to 120 sterile flowers per panicle and about 30 fertile flowers per panicle.

*Panicle height*.—About 12 cm.

*Panicle diameter*.—About 17 cm.

*Sterile flower buds*.—Length: About 2 mm. Diameter: About 2 mm. Shape: Round. Color: Close to 104C.

*Fertile flower buds*.—Length: About 4 mm. Diameter: About 3 mm. Shape: Round. Color: Close to 104C.

*Sterile flower diameter*.—About 5 cm.

*Sterile flower depth* (*height*).—About 6 mm.

*Fertile flower diameter*.—About 5 mm.

*Fertile flower depth* (*height*).—About 5 mm.

*Petals, sterile flowers only, fertile flowers without petals*.—Quantity and arrangement: Four in a single whorl. Length: About 4 mm. Width: About 2 mm. Shape: Ovate. Apex: Acute. Base: Cuneate. Margin: Entire. Texture, upper and lower surfaces: Smooth, glabrous. Color: When opening, upper and lower surfaces: Close to 104C. Fully opened, upper and lower surfaces: Close to 104C; color does not fade with development.

*Sepals, sterile flowers*.—Quantity and arrangement: Four in a single whorl. Length: About 3 cm. Width: About 3.5 cm. Shape: Roughly deltoid. Apex: Retuse. Base: Cuneate. Margin: Entire to slightly crenate. Texture, upper and lower surfaces: Smooth, glabrous. Color: When opening, upper surface: Close to 97B.

When opening, lower surface: Close to 97C. Fully opened, upper surface: Close to 96B; towards the apex, color becoming closer to 80C with development. Fully opened, lower surface: Close to 96C; color becoming closer to 80D with development.

*Sepals, fertile flowers*.—Quantity and arrangement: Four in a single whorl. Length: About 3.5 mm. Width: About 2 mm. Shape: Ovate. Apex: Acute. Base: Attenuate. Margin: Entire. Texture, upper and lower surfaces: Smooth, glabrous. Color: When opening, upper and lower surfaces: Close to 157D. Fully opened, upper and lower surfaces: Close to 95C.

*Pedicels, sterile flowers*.—Length: About 3 cm. Diameter: About 1.5 mm. Strength: Strong. Texture: Smooth, glabrous. Color: Close to 96B.

*Pedicels, fertile flowers*.—Length: About 1 cm. Diameter: About 1 mm. Strength: Strong. Texture: Smooth, glabrous. Color: Close to 98B.

*Reproductive organs*.—Stamens, sterile flowers: Quantity per flower: Eight. Filament length: About 4 mm. Filament color: Close to 96B. Anther shape: Conical. Anther length: About 1 mm. Anther color: Close to 155D. Pollen amount: None observed. Stamens, fertile flowers: Quantity per flower: Eight. Filament length: About 1 mm. Filament color: Close to 98B. Anther shape: Conical. Anther length: About 1 mm. Anther color: Close to 98B. Pollen amount: Abundant. Pollen color: Close to 155D. Pistils, present on fertile flowers only: Pistil quantity per flower: Three. Pistil length: About 1 mm. Stigma shape: Oval. Stigma color: Close to 155A. Style length: About 1 mm. Style color: Close to 101D. Ovary color: Close to 145D.

*Seeds*.—Length: About 0.5 mm. Diameter: About 0.1 mm. Color: Close to 200C.

Disease & pest resistance: Under commercial production conditions, plants of the new *Hydrangea* have not been observed to be resistant to pathogens or pests common to *Hydrangea* plants.

Temperature tolerance: Plants of the new *Hydrangea* have been shown to be tolerant to temperatures ranging from about 3° C. to about 38° C.

It is claimed:

1. A new and distinct *Hydrangea* plant named 'HBAmari' as illustrated and described.

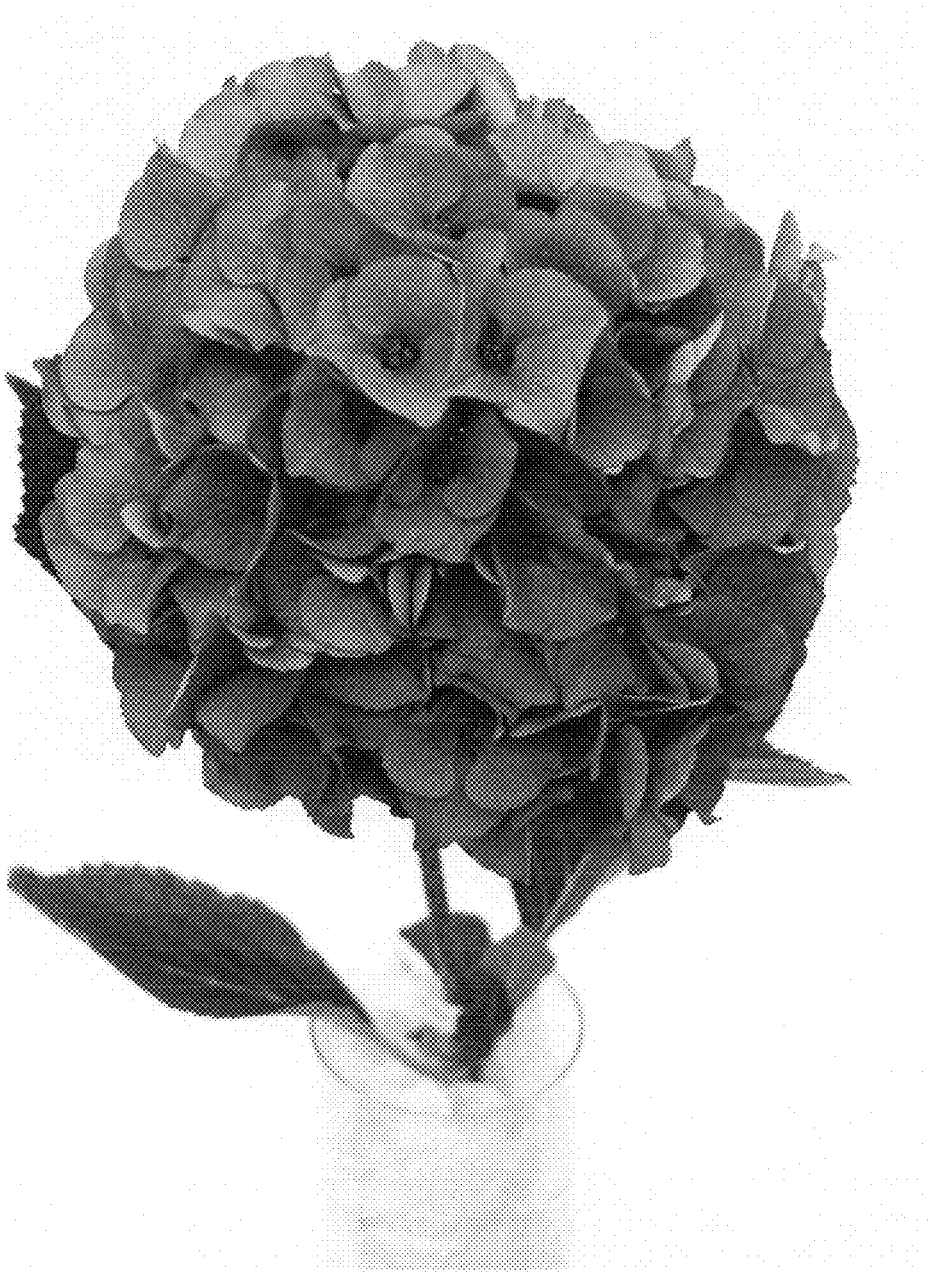

* * * * *